(12) United States Patent
Park et al.

(10) Patent No.: US 11,813,039 B2
(45) Date of Patent: Nov. 14, 2023

(54) APPARATUS AND METHOD FOR ESTIMATING BIO-INFORMATION

(71) Applicant: SAMSUNG ELECTRONICS CO., LTD., Suwon-si (KR)

(72) Inventors: Chang Soon Park, Chungju-si (KR); Ui Kun Kwon, Hwaseong-si (KR); Seung Keun Yoon, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 324 days.

(21) Appl. No.: 16/593,612

(22) Filed: Oct. 4, 2019

(65) Prior Publication Data

US 2020/0275839 A1 Sep. 3, 2020

(30) Foreign Application Priority Data

Feb. 28, 2019 (KR) ........................ 10-2019-0024070

(51) Int. Cl.
*A61B 5/00* (2006.01)
*A61B 5/0215* (2006.01)
*A61B 5/02* (2006.01)

(52) U.S. Cl.
CPC ........ *A61B 5/0059* (2013.01); *A61B 5/02156* (2013.01); *A61B 5/7225* (2013.01); *A61B 5/7275* (2013.01); *A61B 5/02007* (2013.01); *A61B 5/681* (2013.01); *A61B 2560/0223* (2013.01)

(58) Field of Classification Search
CPC . A61B 5/0059; A61B 5/02156; A61B 5/7225; A61B 5/7275; A61B 5/02007; A61B 5/681; A61B 2560/0223

USPC ......................................... 600/310
See application file for complete search history.

(56) References Cited

U.S. PATENT DOCUMENTS

| 9,610,018 | B2 | 4/2017 | Gulati et al. |
| 2016/0374620 | A1 | 12/2016 | Lisogurski et al. |
| 2017/0172431 | A1 | 6/2017 | Kim et al. |
| 2017/0360374 | A1 | 12/2017 | Elliott et al. |
| 2018/0020991 | A1 | 1/2018 | Aung et al. |
| 2018/0125422 | A1 | 5/2018 | Jang et al. |
| 2018/0146899 | A1 | 5/2018 | Lee et al. |
| 2018/0177465 | A1 | 6/2018 | Kwon et al. |

(Continued)

FOREIGN PATENT DOCUMENTS

| JP | 2018-508273 A | 3/2018 |
| KR | 10-1503604 B1 | 3/2015 |

(Continued)

OTHER PUBLICATIONS

Communication dated Apr. 24, 2020 issued by the European Patent Office in counterpart European Application No. 20159501.4.

(Continued)

*Primary Examiner* — Alex M Valvis
*Assistant Examiner* — Chanel J Jhin
(74) *Attorney, Agent, or Firm* — Sughrue Mion, PLLC

(57) ABSTRACT

An apparatus for estimating bio-information includes a sensor configured to measure a bio-signal from an object, and a processor configured to obtain a feature based on the measured bio-signal, obtain a bio-information variation based on the obtained feature, obtain an adjustment coefficient based on the obtained bio-information variation, and estimate the bio-information by applying the obtained adjustment coefficient to the obtained bio-information variation.

18 Claims, 11 Drawing Sheets

(56) References Cited

U.S. PATENT DOCUMENTS

2018/0325398 A1   11/2018   Nitzan
2018/0353089 A1   12/2018   Choi et al.
2019/0038151 A1    2/2019   Lee et al.

FOREIGN PATENT DOCUMENTS

| KR | 10-2017-0067131 A | 6/2017 |
| KR | 10-2017-0073051 A | 6/2017 |
| KR | 10-1746492 B1 | 6/2017 |
| KR | 10-2018-0050946 A | 5/2018 |
| KR | 10-2018-0076806 A | 7/2018 |
| KR | 10-2019-0013319 A | 2/2019 |
| KR | 10-1918577 B1 | 2/2019 |
| WO | 2016096919 A1 | 6/2016 |

OTHER PUBLICATIONS

S Sun et al., "Systolic blood pressure estimation using PPG and ECG during physical exercise", Physiological Measurement, 37, doi: 10.1088/0967-3334/37/12/2154, Nov. 14, 2016, pp. 2154-2169, 16 pages total.

Y. Yoon and G. Yoon, "Nonconstrained Blood Pressure Measurement by Photoplethysmography", Journal of the Optical Society of Korea, vol. 10, No. 2, Jun. 2006, pp. 91-95, (5 pages total).

S. C. Millasseau et al., "The Vascular Impact of Aging and Vasoactive Drugs: Comparison of Two Digital Volume Pulse Measurements", American Journal of Hypertension, 2003, vol. 16, No. 6, pp. 467-472 (6 pages total).

APPARATUS AND METHOD FOR ESTIMATING BIO-INFORMATION

CROSS-REFERENCE TO RELATED APPLICATION

This application claims priority from Korean Patent Application No. 10-2019-0024070, filed on Feb. 28, 2019, in the Korean Intellectual Property Office, the disclosure of which is incorporated herein by reference in its entirety.

BACKGROUND

1. Field

Apparatuses and methods consistent with embodiments relate to technology for estimating bio-information, and more particularly to technology for cufflessly estimating blood pressure.

2. Description of the Related Art

Recently, with the aging population, soaring medical costs, and a lack of medical personnel for specialized medical services, research is being actively conducted on information technology (IT)-medical convergence technologies, in which IT technology and medical technology are combined. Monitoring of the health condition of the human body is not limited to medical institutions, but is expanding to mobile healthcare fields that may monitor a user's health condition anywhere and anytime in daily life at home or office. Examples of bio-signals, which indicate the health condition of individuals, include an electrocardiography (ECG) signal, a photoplethysmogram (PPG) signal, an electromyography (EMG) signal, and the like, and various bio-signal sensors have been developed to measure these signals in daily life. A PPG sensor may estimate blood pressure of a human body by analyzing a shape of pulse waves that reflect cardiovascular status and the like.

According to studies on the PPG signal, the entire PPG signal is a superposition of propagation waves departing from the heart and moving toward the distal portions of the body, and reflection waves returning back from the distal portions. Further, it has been known that information for estimating blood pressure may be obtained by extracting various features associated with the propagation waves or the reflection waves.

SUMMARY

According to an aspect of an example embodiment, there is provided an apparatus for estimating bio-information, the apparatus including a sensor configured to measure a bio-signal from an object, and a processor configured to obtain a feature based on the measured bio-signal, obtain a bio-information variation based on the obtained feature, obtain an adjustment coefficient based on the obtained bio-information variation, and estimate the bio-information by applying the obtained adjustment coefficient to the obtained bio-information variation.

The processor may be further configured to obtain the bio-information variation by multiplying, by a scale factor, a variation of the obtained feature in comparison to a feature that is obtained at a reference time.

The processor may be further configured to obtain the adjustment coefficient based on the obtained bio-information variation, using an adjustment coefficient function.

The adjustment coefficient function may output the adjustment coefficient to be applied to the obtained bio-information variation to adjust the obtained bio-information variation so that the bio-information variation is closer to a reference bio-information variation.

The adjustment coefficient function may be defined such that as an absolute value of the bio-information variation decreases, the adjustment coefficient has an increasing trend, and as the absolute value of the bio-information variation increases, the adjustment coefficient decreases or has a constant value after a predetermined point of the absolute value of the bio-information variation.

The adjustment coefficient function may be defined using either one or both of a linear function and a non-linear function for intervals that are divided based on either one or both of a sign and a magnitude of the bio-information variation.

The adjustment coefficient function may be defined such that, in an interval in which the bio-information variation has a negative sign and the magnitude of the bio-information variation is less than a first threshold, the adjustment coefficient is maintained at a first value, in an interval in which the bio-information has the negative sign and the magnitude of the bio-information variation ranges from the first threshold to a second threshold greater than the first threshold, the adjustment coefficient linearly or non-linearly increases from the first value to a second value, in an interval in which the bio-information has the negative sign and the magnitude of the bio-information variation ranges from the second threshold to zero, the adjustment coefficient is maintained at the second value, or linearly or non-linearly increases from the second value to a third value, in an interval in which the bio-information variation has a positive sign and the magnitude of the bio-information variation ranges from zero to a third threshold, the adjustment coefficient is maintained at a fourth value, or linearly or non-linearly decreases from the fourth value to a fifth value, in an interval in which the bio-information has the positive sign and the magnitude of the bio-information variation ranges from the third threshold to a fourth threshold greater than the third threshold, the adjustment coefficient linearly or non-linearly decreases from the fourth value to a sixth value or from the fifth value to the sixth value, and in an interval in which the bio-information has the positive sign and the magnitude of the bio-information variation is greater than the fourth threshold, the adjustment coefficient is maintained at the sixth value.

Each of the first threshold, the second threshold, the third threshold, the fourth threshold, the first value, the second value, the third value, the fourth value, the fifth value, the sixth value, the linear function and the non-linear function are defined based on any one or any combination of a computing performance, types of the bio-information to be estimated, user characteristics, and a surrounding environment.

The processor may be further configured to obtain a bio-information estimation value by multiplying the obtained bio-information variation by the obtained adjustment coefficient and by adding an offset to the bio-information variation multiplied by the obtained adjustment coefficient.

The processor may be further configured to obtain the feature by combining any or any combination of a shape of a waveform of the measured bio-signal, a time value and an amplitude value of a maximum point of the measured bio-signal, a time value and an amplitude value of a minimum point of the measured bio-signal, a time value and an amplitude value of a position of a pulse waveform component included in the measured bio-signal, and an area of the measured bio-signal.

The sensor may include a light source configured to emit light onto the object, and a detector configured to detect light that is scattered from the object.

The bio-information may include any one or any combination of a blood pressure, a vascular compliance, an arterial stiffness, a stress index, a degree of fatigue, a skin elasticity, and a skin age.

According to an aspect of another example embodiment, there is provided a method of estimating bio-information, the method including measuring a bio-signal from an object, obtaining a feature based on the measured bio-signal, obtaining a bio-information variation based on the obtained feature, obtaining an adjustment coefficient based on the obtained bio-information variation, and estimating the bio-information by applying the obtained adjustment coefficient to the obtained bio-information variation.

The obtaining of the bio-information variation may include obtaining the bio-information variation by multiplying, by a scale factor, a variation of the obtained feature in comparison to a feature that is obtained at a reference time.

The obtaining of the adjustment coefficient may include obtaining the adjustment coefficient based on the obtained bio-information variation, using an adjustment coefficient function.

The adjustment coefficient function may output the adjustment coefficient to be applied to the obtained bio-information variation to adjust the obtained bio-information variation so that the bio-information variation is closer to a reference bio-information variation.

The adjustment coefficient function may be defined such that as an absolute value of the bio-information variation decreases, the adjustment coefficient has an increasing trend, and as the absolute value of the bio-information variation increases, the adjustment coefficient decreases or has a constant value after a predetermined point of the absolute value of the bio-information variation.

The adjustment coefficient function may be defined using either one or both of a linear function and a non-linear function for intervals that are divided based on either one or both of a sign and a magnitude of the bio-information variation.

The estimating of the bio-information may include obtaining a bio-information estimation value by multiplying the obtained bio-information variation by the obtained adjustment coefficient and by adding an offset to the bio-information variation multiplied by the obtained adjustment coefficient.

The obtaining of the feature may include obtaining the feature by combining any or any combination of a shape of a waveform of the measured bio-signal, a time value and an amplitude value of a maximum point of the measured bio-signal, a time value and an amplitude value of a minimum point of the measured bio-signal, a time value and an amplitude value of a position of a pulse waveform component included in the measured bio-signal, and an area of the measured bio-signal.

According to an aspect of another example embodiment, there is provided an apparatus for estimating bio-information, the apparatus including a sensor configured to measure a bio-signal from an object, and a processor configured to obtain a feature based on the measured bio-signal, obtain a bio-information variation based on the obtained feature, determine a mode for obtaining an adjustment coefficient, based on calibration information items, based on the mode for obtaining the adjustment coefficient being determined to be an on mode, obtain the adjustment coefficient based on the obtained bio-information variation, and estimate the bio-information by applying the obtained adjustment coefficient to the obtained bio-information variation.

The processor may be further configured to, based on the mode for obtaining the adjustment coefficient being determined to be an off mode, estimate the bio-information based on the obtained bio-information variation, without obtaining the adjustment coefficient, and, based on the mode for obtaining the adjustment coefficient being determined to be a shape change mode, change an adjustment coefficient function, and obtain the adjustment coefficient based on the obtained bio-information variation, using the changed adjustment coefficient function.

The calibration information items may include a number of times that calibration is performed before a current time of estimating the bio-information, and based on calibrations being performed, a level of change between reference bio-information values that are obtained at each of the calibrations and/or a level of change between features that are obtained based on the bio-signal measured at each of the calibrations.

The processor may be further configured to, based on the number of times that the calibration is performed before the current time of estimating the bio-information being less than a threshold, determine the mode for obtaining the adjustment coefficient to be the off mode, and based on the number of times that the calibration is performed before the current time of estimating the bio-information being greater than or equal to the threshold, determine the mode for obtaining the adjustment coefficient to be the on mode.

The processor may be further configured to, based on any one or any combination of the calibration information items being less than a threshold, determine the mode for obtaining the adjustment coefficient to be the shape change mode.

The processor may be further configured to, based on the mode for obtaining the adjustment coefficient being determined to be the shape change mode, change a shape of the adjustment coefficient function so that the adjustment coefficient is similar to a constant value of 1.

The processor may be further configured to, based on any one or any combination of the calibration information items being less than a first threshold, determine the mode for obtaining the adjustment coefficient to be the off mode, based on any one or any combination of the calibration information items being greater than or equal to the first threshold and less than a second threshold, determine the mode for obtaining the adjustment coefficient to be the shape change mode, and based on any one or any combination of the calibration information items being greater than or equal to the second threshold, determine the mode for obtaining the adjustment coefficient to be the on mode.

According to an aspect of another example embodiment, there is provided a method of estimating bio-information, the method including measuring a bio-signal from an object, obtaining a feature from the measured bio-signal, obtaining a bio-information variation based on the obtained feature, determining a mode for obtaining an adjustment coefficient, based on calibration information items, based on the mode for obtaining the adjustment coefficient being determined to be an on mode, obtaining the adjustment coefficient based on the obtained bio-information variation, based on the mode for obtaining the adjustment coefficient being determined to be a shape change mode, changing an adjustment coefficient function, and obtaining the adjustment coefficient based on the obtained bio-information variation, using the changed adjustment coefficient function, and estimating the bio-information by applying the obtained adjustment coefficient to the obtained bio-information variation.

The determining the mode for obtaining the adjustment coefficient may include, based on a level of change between reference bio-information values that are obtained at each of calibrations and/or a level of change between features that are obtained from the bio-signal measured at each of the calibrations, being less than a threshold, determine the mode for obtaining the adjustment coefficient to be the on mode.

The determining the mode for obtaining the adjustment coefficient may include, based on a number of times that calibration is performed before a current time of the estimating of the bio-information, being greater than or equal to a threshold and being increased, determine the mode for obtaining the adjustment coefficient to be the shape change mode in which a shape of the adjustment coefficient function is changed to a narrower or sharper shape adjacent to a point at which the bio-information variation is zero.

BRIEF DESCRIPTION OF THE DRAWINGS

The above and/or other aspects will become apparent and more readily appreciated from the following description of example embodiments, taken in conjunction with the accompanying drawings in which.

DETAILED DESCRIPTION

Figure 1A:
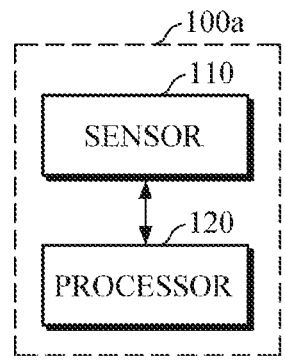
FIGS. 1A and 1B are block diagrams illustrating an apparatus for estimating bio-information according to example embodiments.

Details of example embodiments are included in the following detailed description and drawings. Advantages and features of the example embodiments, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements may not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., may be understood as a unit that performs at least one function or operation and that may be embodied as hardware, software, or a combination thereof.

Hereinafter, embodiments of an apparatus and method for estimating bio-information will be described in detail with reference to the accompanying drawings.

Figure 1B:
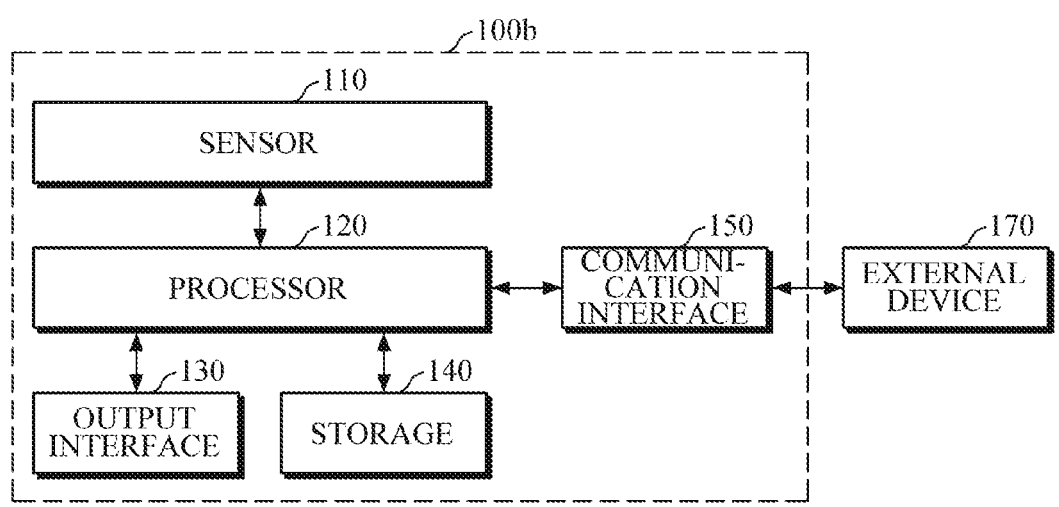

FIGS. 1A and 1B are block diagrams illustrating an apparatus for estimating bio-information according to example embodiments. The bio-information estimating apparatuses 100a and 100b may be embedded in a terminal such as a smartphone, a tablet PC, a desktop computer, a laptop computer, and the like, or in a wearable device that may be worn on an object. In this case, examples of a wearable device may include a wristwatch-type wearable device, a bracelet-type wearable device a wristband-type wearable device, a ring-type wearable device, a glasses-type wearable device, a headband-type wearable device and the like. However, the wearable device is not limited thereto, and may also be embedded in a medical device manufactured for use in medical institutions to measure and analyze bio-information.

Referring to FIGS. 1A and 1B, the bio-information estimating apparatuses 100a and 100b include a sensor 110 and a processor 120.

The sensor 110 may measure a bio-signal from an object. In this case, the bio-signal may include a photoplethysmogram (PPG) signal. However, the bio-signal is not limited thereto, and may include various bio-signals, such as an electrocardiography (ECG) signal, a photoplethysmogram (PPG) signal, an electromyography (EMG) signal, and the like, which may be modeled by a sum of a plurality of waveform components. In this case, the object may be a body part that comes into contact with or is adjacent to the sensor 110, and may be a body part where pulse waves may be easily measured. For example, the object may be an area of skin on the wrist that is adjacent to the radial artery or a human skin area where veins or capillaries pass. However, the object is not limited thereto, and may be peripheral body portions, such as fingers, toes, and the like, which have a high density of blood vessels.

The sensor 110 may include a light source and a detector. The light source may emit light onto the object, and the detector may detect light scattered or reflected from the object. The light source may include a light emitting diode (LED), a laser diode (LD), a fluorescent body, and the like, and may be formed in one or two or more arrays. The detector may include one or more pixels, each of which includes a photo diode, a photo transistor (PTr), an image sensor, and the like, which detects light and converts the detected light into an electric signal.

The processor 120 may be electrically connected to the sensor 110. The processor 120 may control the sensor 110 in response to a request for estimating bio-information, and may receive a bio-signal from the sensor 110. The request for estimating bio-information may be input by a user, or may be generated at predetermined intervals. Upon receiving an electrical bio-signal from the sensor 110, the processor 120 may perform preprocessing such as filtering for removing noise, amplifying the bio-signal, converting the bio-signal into a digital signal, and the like.

The processor 120 may estimate bio-information based on the bio-signal received from the sensor 110. In this case, bio-information may include blood pressure, vascular compliance, arterial stiffness, stress index, degree of fatigue, skin elasticity, skin age, and the like. Hereinafter, the following description will be given using blood pressure as an example.

The processor 120 may obtain a feature, having a high correlation with bio-information, by analyzing the bio-signal, and may estimate bio-information based on the obtained feature. For example, the processor 120 may obtain a bio-information variation by applying a scale factor to a variation of a feature (hereinafter referred to as a "feature variation) that is obtained from a bio-signal at an estimation time (hereinafter referred to as an "estimation feature") compared to a feature (hereinafter referred to as a "reference feature") that is obtained from a bio-signal at a reference time (e.g., calibration time), and may estimate bio-information based on the obtained bio-information variation.

For example, the following Equation 1 shows an example of an equation for estimating bio-information.

$$est = SF \times (f - f_{cal}) + ref_{cal} \quad \text{[Equation 1]}$$

Herein, est denotes a bio-information estimation value, f denotes an estimated feature, $f_{cal}$ denotes a reference feature, and $ref_{cal}$ denotes bio-information obtained at the reference time by an external bio-information measuring device. In this case, $(f - f_{cal})$ may indicate the variation of the feature at the estimation time compared to the feature at the reference time.

As described above, the processor 120 may obtain the bio-information estimation value by multiplying the feature variation by the scale factor, and by adding an offset to reference bio-information at the reference time. A feature, obtained from a bio-signal, is a value that changes by reflecting characteristics of the bio-signal at a measurement time for each individual, but the scale factor for scaling the feature variation is a fixed constant value that is applied, such that the scale factor may not sufficiently reflect circumstances in which a magnitude of the variation of bio-information compared to the feature at the calibration time is changed to various values due to various individual characteristics, surrounding environments, and the like.

Accordingly, in an example embodiment, the processor 120 may further obtain an adjustment coefficient for adaptively adjusting the scale factor as will be described later with reference to FIG. 2, and may estimate bio-information more accurately by applying the obtained adjustment coefficient.

Referring to FIG. 1B, the bio-information estimating apparatus 100b includes an output interface 130, a storage 140, and a communication interface 150.

The output interface 130 may output a result processed by the sensor 110 and the processor 120. For example, the output interface 130 may visually output a bio-information estimation value through a display. Alternatively, the output interface 130 may output the value in a non-visual manner through voice, vibrations, tactile sensation, and the like by using a speaker, a haptic interface, and the like. The output interface 130 may divide a display area into two or more areas according to a predetermined setting, in which the output interface 130 may output a bio-signal graph used for estimating bio-information, a bio-information estimation result, and the like in a first area; and may output a bio-information estimation history in the form of graphs and the like in a second area. In this case, if the bio-information estimation value falls outside a normal range, the output interface 130 may output warning information in various manners, such as highlighting an abnormal value in red and the like, displaying the abnormal value along with a normal range, outputting a voice warning message, adjusting a vibration intensity, and the like.

The storage 140 may store a processing result of the sensor 110 and the processor 120. Further, the storage 140 may store various types of reference information for estimating bio-information. For example, the reference information may include user characteristic information such as a user's age, sex, health condition, and the like. In addition, the reference information may include a reference feature at a calibration time, reference bio-information, a bio-information estimation interval, criteria for determining calibration, an adjustment coefficient function, and the like, but is not limited thereto.

In this case, the storage 140 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 150 may communicate with an external device 170 by using wired or wireless communication techniques under the control of the processor 120, and may transmit and receive various data to and from the external device 170. For example, the communication interface 150 may transmit a bio-information estimation result to the external device 170, and may receive, from the external device 170, various types of reference information such as reference bio-information, an adjustment coefficient function, and the like that are for estimating bio-information. In this case, the external device 170 may include a cuff-type blood pressure measuring device and the like as a bio-information measuring device. Further, the external device 170 may include an information processing device such as a smartphone, a tablet PC, a desktop computer, a laptop computer, and the like.

In this case, examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, these are examples and are not intended to be limiting.

Figure 2:
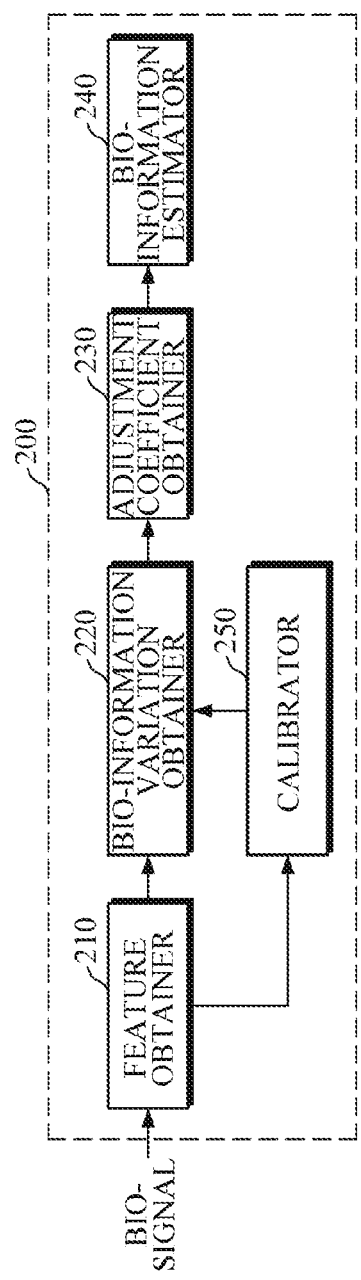
FIG. 2 is a block diagram illustrating an example of a processor of FIGS. 1A and 1B.
Figure 3:
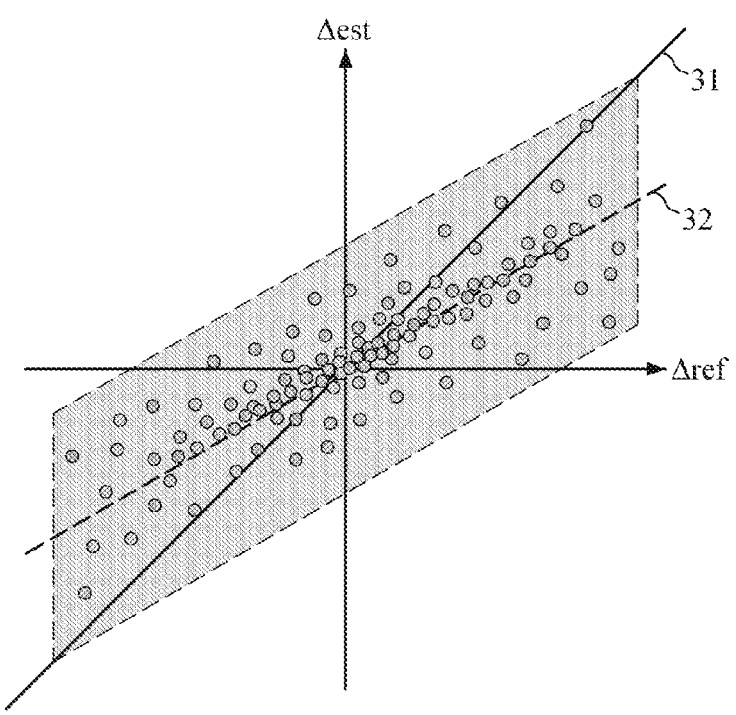
FIG. 3 is a diagram explaining a relationship between an estimated blood pressure variation and an actual blood pressure variation.
Figure 4A:
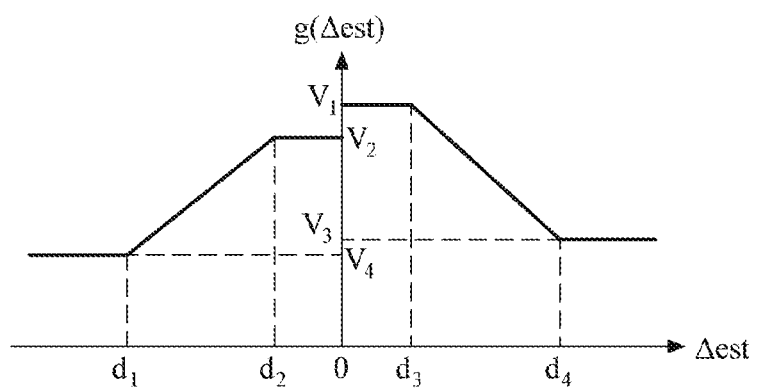
FIGS. 4A and 4B are diagrams illustrating examples of an adjustment coefficient function.
Figure 4B:
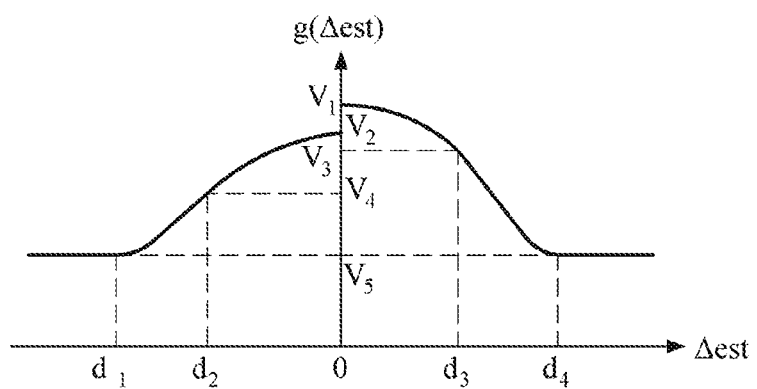

FIG. 2 is a block diagram illustrating an example of a processor of FIGS. 1A and 1B; FIG. 3 is a diagram explaining a relationship between an estimated blood pressure variation and an actual blood pressure variation; and FIGS. 4A and 4B are diagrams illustrating examples of an adjustment coefficient function.

Referring to FIG. 2, the processor 200 includes a feature obtainer 210, a bio-information variation obtainer 220, an adjustment coefficient obtainer 230, a bio-information estimator 240, and a calibrator 250.

The feature obtainer 210 may obtain a feature by analyzing a bio-signal received from the sensor 110. In this case, the feature may be a value having a high correlation with an actual bio-information value, and may be a feature value having the characteristic of increasing/decreasing in the same direction as a direction of increase or decrease in blood pressure. A pulse wave signal may be formed by a superposition of propagation waves departing from the heart and moving toward the distal portions of the body, and reflection waves returning back from the distal portions. By properly combining time and amplitude values of positions of each of the pulse waveform components included in the pulse wave signal, the feature obtainer may extract a feature having a high correlation with blood pressure.

For example, the feature obtainer 210 may extract, from the bio-signal, a shape of a waveform of the bio-signal, a time value and an amplitude value of a maximum point, a time value and an amplitude value of a minimum point, a time value and an amplitude value of the position of the pulse waveform component included in the bio-signal, and an area of one or more intervals of the bio-signal, a heart rate, and the like, and may obtain the feature by properly combining the extracted values. In this case, the feature obtainer 210 may perform secondary differentiation on the bio-signal to obtain the position of the pulse waveform component included in the bio-signal, and may detect a local minimum point of the secondary differential signal to determine the position of the local minimum point to be the position of the pulse waveform component. Alternatively, the feature obtainer 210 may obtain a new feature by properly combining two or more of the feature values. In this case, the feature obtainer 210 may combine the feature values in various manners, such as addition, subtraction, division, multiplication, logarithmic value, and a combination thereof, but is not specifically limited thereto.

The bio-information variation obtainer 220 may obtain a bio-information variation based on the feature obtained by the feature obtainer 210. In this case, the bio-information variation is a value that indicates an increase or decrease in a bio-information estimation value at a current estimation time as compared to a reference bio-information value measured at a reference time (e.g., calibration time). That is, by reference to the above Equation 1, the bio-information variation $\Delta$est may be SF×(f−$f_{cal}$), which is a value obtained by multiplying the feature variation by the scale factor.

FIG. 3 is a diagram illustrating a scatter plot showing a relationship between a reference blood pressure variation $\Delta$ref at a bio-information estimation time compared to a calibration time (i.e., a value obtained by subtracting a reference blood pressure value at the calibration time from a reference blood pressure at the estimation time), and an estimated blood pressure variation $\Delta$est (i.e., a value obtained by subtracting a feature at the calibration time from a feature at the estimation time and multiplying the subtracted value by the scale factor). As illustrated in FIG. 3, with respect to a reference blood pressure variation $\Delta$ref, the estimated blood pressure variation $\Delta$est is distributed vertically with noise included therein. To improve total error performance, a linear straight line 32 in the scatter plot of the estimated blood pressure variation $\Delta$est compared to the reference blood pressure variation $\Delta$ref has a smaller value than a straight line 31 having a slope of 1. If all the points are positioned only on the straight line 31 having the slope of 1, this corresponds to a case in which there is no error at all.

When bio-information including blood pressure is estimated, an error performance in an interval may be improved, in which a variation of bio-information is large, than to improve error performance in an interval in which a variation of bio-information is small. For example, when blood pressure is continuously monitored during daily activities, it is considered more dangerous when blood pressure changes significantly than when blood pressure changes slightly. Accordingly, to manage and prevent danger to a user's health, accuracy in estimating blood pressure may be secured when there is a significant change in blood pressure. However, in a region having a large reference blood pressure variation $\Delta$ref, i.e., a region where a reference blood pressure mostly changes, the accuracy in estimating blood pressure may be gradually reduced. In other words, when observing each point in a region having a large reference blood pressure variation $\Delta$ref, a vertical distance and a horizontal distance are gradually further away from the straight line 31 having the slope of 1.

By considering these circumstances, the adjustment coefficient obtainer 230 may obtain an adjustment coefficient to adaptively adjust the scale factor for scaling a feature variation. In this case, the adjustment coefficient obtainer 230 may obtain the adjustment coefficient based on the bio-information variation obtained by the bio-information variation obtainer 220. That is, the adjustment coefficient may be a value for adjusting the estimated bio-information variation based on the feature obtained from the bio-signal, so that the estimated bio-information variation may be closer to the reference bio-information variation.

The adjustment coefficient obtainer 230 may obtain the adjustment coefficient by using a pre-defined adjustment coefficient function. The adjustment coefficient function may be a linear function, a non-linear function, or a combination thereof, which gradually increases the adjustment coefficient as an absolute value of the bio-information variation relatively decreases, and decreases the adjustment coefficient or maintains the adjustment coefficient at a constant value as the absolute value relatively increases. For example, the adjustment coefficient function may be defined for each of a plurality of intervals that are divided in consideration of a sign or a magnitude of a bio-information variation. The adjustment coefficient function may be defined such that the adjustment coefficient may have a decreasing trend as the absolute value of the bio-information variation gradually increases, but the adjustment coefficient function is not limited thereto, and may also be defined such that the adjustment coefficient may increase by a predetermined level in at least some intervals. In this case, the number and range of intervals, information on whether the adjustment coefficient increases or decreases in each interval, the types of linear/non-linear function applied to each interval, and the like may be defined variously by considering computing performance of the apparatus, the types of bio-information to be obtained, the types of bio-signals, individual characteristics of each user, surrounding environments, and the like.

FIGS. 4A and 4B are diagrams illustrating examples of an adjustment coefficient function defined for each predetermined interval according to a magnitude of an estimated bio-information variation $\Delta$est. As illustrated in FIGS. 4A and 4B, the adjustment coefficient function g($\Delta$est) uses the estimated bio-information value $\Delta$est as an input, and may output an adjustment coefficient that adaptively changes according to a sign or a magnitude of the estimated bio-information variation $\Delta$est. As illustrated therein, the adjustment coefficient function g($\Delta$est) may be defined using a linear/non-linear function that outputs an adjustment coefficient having a high value as an absolute value of the estimated bio-information variation $\Delta$est decreases, and outputs an adjustment coefficient having a value that gradually decreases or an equal/similar value as an absolute value of the estimated bio-information variation $\Delta$est increases.

As illustrated in FIG. 4A, an example of the adjustment coefficient function g($\Delta$est) may be defined using a linear function for each interval of the estimated bio-information variation Δest, so that each interval of the estimated bio-information variation test may have a linear straight line or may have the same constant value.

For example, the adjustment coefficient function may be defined such that when the bio-information variation Δest gradually decreases from zero, i.e., when the bio-information variation Δest gradually decreases in an interval in which the bio-information variation Δest has a negative sign (−), the adjustment coefficient may also have a gradually decreasing trend. For example, the adjustment coefficient function may be defined such that in a first interval in which the bio-information variation Δest is less than a first threshold $d_1$, the adjustment coefficient function may be maintained at a first value $v_4$. However, the adjustment coefficient function is not limited thereto, and may be defined such that as the bio-information variation Δest gradually decreases in the first interval, the adjustment coefficient may also decrease/increase slightly. Further, the adjustment coefficient function may be defined such that in a second interval in which the bio-information variation test ranges between a second threshold $d_2$ and the first threshold $d_1$, the adjustment coefficient may linearly decrease from a second value $v_2$ to the first value $v_4$ as the bio-information variation Δest gradually decreases. In addition, the adjustment coefficient function may be defined such that in a third interval in which the bio-information variation Δest ranges between zero and the second threshold $d_2$, the adjustment coefficient may be maintained at the second value $v_2$. However, the adjustment coefficient function is not limited thereto, and may be defined such that the adjustment coefficient may decrease/increase slightly and linearly from a third value to the second value $v_2$. In this case, a range of increase/decrease from the third value to the second value $v_2$ may be set to be relatively smaller than a range of decrease of the second interval.

Further, the adjustment coefficient function may be defined such that when the bio-information variation Δest gradually increases from zero, i.e., when the bio-information variation Δest gradually increases in an interval in which the bio-information variation Δest has a positive sign (+), the adjustment coefficient may have a gradually decreasing trend. For example, the adjustment coefficient function may be defined such that in a fourth interval in which the bio-information variation Δest ranges between zero and a third threshold $d_3$, the adjustment coefficient may be maintained at a fourth value $v_1$. However, the adjustment coefficient function is not limited thereto, and may be defined such that the adjustment coefficient may decrease/increase slightly and linearly from the fourth value $v_1$ to a fifth value in the fourth interval. Further, the adjustment coefficient function may be defined such that in a fifth interval in which the bio-information variation Δest ranges between the third threshold $d_3$ and a fourth threshold $d_4$, the adjustment coefficient may linearly decrease from the fourth value $v_1$ or the fifth value to a sixth value $v_3$. In addition, the adjustment coefficient function may be defined such that in a sixth interval in which the bio-information variation Δest is greater than or equal to the fourth threshold $d_4$, the adjustment coefficient may be maintained at the sixth value $v_3$. In this case, a range of decrease from the fourth value $v_1$ to the fifth value may be set to be relatively smaller than a range of decrease from the fifth value to the sixth value $v_3$.

Furthermore, the second value $v_2$ and the fourth value $v_1$ may be set to be equal to each other; the first value $v_4$ and the sixth value $v_3$ may also be set to be equal to each other; and the adjustment coefficient function may be defined to be symmetric based on zero.

As illustrated in FIG. 4B, another example of the adjustment coefficient function g Δest may be defined using non-linear functions for at least some intervals of the estimated bio-information variation test, so that each interval of the estimated bio-information variation Δest may have a non-linear shape or may have the same constant value.

For example, the adjustment coefficient function may be defined such that when the bio-information variation Δest gradually decreases from zero, i.e., when the bio-information variation Δest decreases in an interval in which the bio-information variation test has a negative sign (−), the adjustment coefficient may also have a gradually decreasing trend. For example, the adjustment coefficient function may be defined such that in the first interval in which the bio-information variation Δest is less than the first threshold $d_1$, the adjustment coefficient may be maintained at a first value $v_5$. However, the adjustment coefficient function is not limited thereto, and may be defined such that as the bio-information variation Δest gradually decreases in the first interval, the adjustment coefficient may also decrease/increase slightly. Further, the adjustment coefficient function may be defined such that as the bio-information variation Δest decreases in the second interval, in which the bio-information variation Δest ranges between the second threshold $d_2$ and the first threshold $d_1$, the adjustment coefficient may non-linearly decrease from a second value $v_4$ to the first value $v_5$. In addition, the adjustment coefficient function may be defined such that in the third interval in which the bio-information variation Δest ranges between zero and the second threshold $d_2$, the adjustment coefficient may non-linearly decrease from a third value $v_2$ to the second value $v_4$. However, the adjustment coefficient function is not limited thereto, and may be defined linearly so that the adjustment coefficient may be maintained at the second value $v_4$ in the third interval. In this case, a range of decrease between the third value $v_2$ and the second value $v_4$ may be set to be relatively smaller than a range of decrease between the second value $v_4$ and the first value $v_5$.

Further, the adjustment coefficient function may be defined such that when the bio-information variation Δest gradually increases from zero, i.e., when the bio-information variation Δest gradually increases in an interval in which the bio-information variation Δest has a positive sign (+), the adjustment coefficient may have a gradually decreasing trend. For example, the adjustment coefficient function may be defined such that in the fourth interval in which the bio-information variation Δest ranges between zero and the third threshold $d_3$, the adjustment coefficient may non-linearly decrease from the fourth value $v_1$ to the fifth value $v_3$. However, the adjustment coefficient function is not limited thereto, and may be defined linearly so that the adjustment coefficient may be maintained at the fourth value $v_1$ in the fourth interval. Further, the adjustment coefficient function may be defined such that in the fifth interval, in which the bio-information variation Δest ranges between the third threshold $d_3$ to the fourth threshold $d_4$, the adjustment coefficient may non-linearly decrease from the fifth value $v_3$ to a sixth value $v_5$. In addition, the adjustment coefficient function may be defined such that in the sixth interval, in which the bio-information variation Δest is greater than the fourth threshold $d_4$, the adjustment coefficient may be maintained at the sixth value $v_5$. In this case, a range of decrease between the fourth value $v_1$ and the fifth value $v_3$ may be set to be relatively smaller than a range of decrease between the fifth value $v_3$ and the sixth value $v_5$.

Furthermore, the first value $v_5$ and the sixth value $v_5$, the second value $v_4$ and the fifth value $v_3$, and the third value $v_2$ and the fourth value $v_2$ may be set to equal to each other. In addition, the adjustment coefficient function may be defined so that the values may be symmetric to each other based on zero. In this case, the non-linear function may include a function obtained by connecting different second-order polynomial equations, a Gaussian function, a logarithmic function, and the like.

However, the adjustment coefficient function is not limited to the examples of FIGS. 4A and 4B, and the number of intervals may be increased/decreased based on computing performance of the apparatus, individual characteristics of users, types of bio-information to be estimated, and the like, and each threshold and each value may be defined differently. Further, as in the case of combining FIGS. 4A and 4B, an adjustment coefficient function may be defined by using a linear function in an interval and a non-linear function in another interval.

Once the adjustment coefficient obtainer 230 obtains the adjustment coefficient for adjusting the scale factor, the bio-information estimator 240 may estimate bio-information by further applying an adjustment coefficient to a bio-information variation, to which the scale factor is applied. For example, the following Equation 2 represents an equation for estimating bio-information, which is obtained by further applying an adjustment coefficient to the above Equation 1 for estimating bio-information.

$$\text{est\_final} = g(\Delta \text{est}) \times SF \times (f - f_{cal}) + \text{ref}_{cal} \quad \text{[Equation 2]}$$

Herein, est_final denotes a final bio-information estimation value to be obtained; gΔest is an output value of the adjustment coefficient function and denotes the adjustment coefficient; SF denotes the scale factor; f denotes the feature at the estimation time; and $f_{cal}$ denotes the feature at the reference time. In this case, an estimated bio-information variation is a value obtained by multiplying a feature variation $f - f_{cal}$, which is obtained by subtracting the feature at the reference time from the feature at the estimation time, by the scale factor SF; and by multiplying the estimated bio-information variation by the adjustment coefficient value gΔest for adjusting the scale factor, the estimated bio-information variation may be adjusted to be closer to an actual bio-information variation. In addition, $\text{ref}_{cal}$ denotes an offset to be added to the adjusted bio-information variation, and may be an actual bio-information value that is measured by an external bio-information measuring device at a reference time (e.g., calibration time).

As described above, bio-information may be estimated more accurately by obtaining a value by multiplying a scale factor, which is a fixed constant value that is applied, by an adjustment coefficient that is obtained adaptively based on a magnitude of the bio-information variation, and by using the value as a new scale factor for scaling the feature variation.

The calibrator 250 may perform calibration upon receiving a user's request for calibration or if predetermined criteria for calibration are satisfied. In the case in which the predetermined criteria for calibration are satisfied, the calibrator 250 may guide a user to perform calibration. For example, at predetermined calibration intervals, or if a total number of times that bio-information estimation values fall outside a normal range, a number of times that bio-information estimation values continue to fall outside a normal range, or a number of times that bio-information estimation values fall outside a normal range during a predetermined period of time is greater than or equal to a predetermined threshold, the calibrator 250 may determine that calibration is performed.

Once a user measures reference bio-information using an external bio-information measuring device, the calibrator 250 may receive the reference bio-information from the external bio-information measuring device or the user.

Further, the calibrator 250 may control the sensor 110 to measure a reference bio-signal for calibration. The calibrator 250 may obtain a reference feature from the bio-signal.

In addition, the calibrator 250 may store the obtained reference feature, the reference bio-information, and the like in the storage 140.

Figure 5:
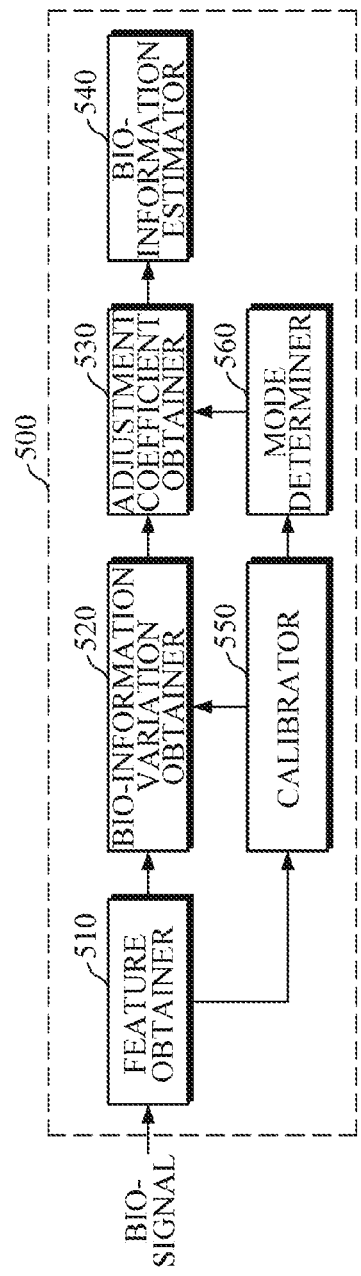
FIG. 5 is a block diagram illustrating another example of a processor of FIGS. 1A and 1B.

FIG. 5 is a block diagram illustrating another example of a processor of FIGS. 1A and 1B.

Referring to FIG. 5, the processor 500 includes a feature obtainer 510, a bio-information variation obtainer 520, an adjustment coefficient obtainer 530, a bio-information estimator 540, a calibrator 550, and a mode determiner 560. Here, the feature obtainer 510, the bio-information variation obtainer 520, the adjustment coefficient obtainer 530, the bio-information estimator 540, and the calibrator 550 are described above in detail with reference to FIG. 2 and the following figures, such that the following description will be given based on non-overlapping parts.

When calibration is performed, the calibrator 550 may generate calibration information, and may update and manage the generated calibration information in the storage 140.

For example, when calibration is performed, the calibrator 550 may update and manage the number of times calibration is performed.

In another example, when calibration is performed, the calibrator 550 may obtain a level of change of reference bio-information (e.g., cuff pressure) measured by an external bio-information measuring device at each calibration time, and may update and manage the level of change of reference bio-information in the storage 140. In this case, the level of change of the reference bio-information may include a statistical value (e.g., a mean value, a median value, a standard deviation, a maximum value, a minimum value, variance, etc.) of difference values between any one bio-information value, which is used as a reference among a plurality of reference bio-information values, and the remaining reference bio-information values.

In another example, when calibration is performed, the calibrator 550 may obtain a level of change of reference features obtained from bio-signals measured by the sensor 110 at each calibration time, and may update and manage the level of change of reference features in the storage 140. In this case, the level of change of reference features may include a statistical value (e.g., a mean value, a median value, a standard deviation, a maximum value, a minimum value, variance, etc.) of difference values between any one reference feature, which is used as a reference among a plurality of reference features, and the remaining reference features.

The mode determiner 560 may determine a mode for obtaining an adjustment coefficient based on the calibration information. In this case, the mode may include either one or both of an on/off mode for controlling turning ON/OFF of operation of the adjustment coefficient obtainer 530, and a shape change mode for adjusting the shape of an adjustment coefficient function. In this case, the calibration information may include a number of times of calibration performed before a current time of estimating bio-information; and when calibration is performed a plurality of times, the calibration information may include a level of change between reference bio-information values obtained at each calibration and a level of change between features obtained from the bio-signal measured at each calibration.

For example, if a number of times of calibration performed before a current time of estimating bio-information is less than a predetermined threshold (e.g., 3 times), the mode determiner 560 may set an OFF mode so that the adjustment coefficient obtainer 530 may not perform a process of obtaining an adjustment coefficient. In this case, the adjustment coefficient obtainer 530 does not perform the process of obtaining an adjustment coefficient, such that bio-information may be estimated in the same manner as the above Equation 1. Further, if a number of times of calibration performed before a current time of estimating bio-information is greater than or equal to a predetermined threshold, the mode determiner 560 may set an ON mode so that the adjustment coefficient obtainer 530 may obtain an adjustment coefficient as described above, and may estimate bio-information in the same manner as the above Equation 2.

In addition, the mode determiner 560 may refer to the storage 140; and if the level of change between the reference bio-information values (e.g., cuff pressure) is less than a predetermined threshold, the mode determiner 560 may set an ON mode. Furthermore, upon referring to the storage 140, if the level of change between reference features updated by the calibrator 550 is less than a predetermined threshold, the mode determiner 560 may set an ON mode.

In another example, the mode determiner 560 may determine a shape change mode of the adjustment coefficient function based on the calibration information. For example, if a number of times of calibration is less than a threshold, the mode determiner 560 may determine that an effect of calibration is not sufficient, and may determine a function shape change mode, to change the shape of the adjustment coefficient function so that the adjustment coefficient may be closer to a constant value of 1. Further, if a number of times of calibration is greater than or equal to a threshold, the mode determiner 560 may not determine a function shape change mode so that a pre-defined adjustment coefficient function may be used as it is. In addition, if a number of times of calibration is greater than or equal to a threshold and is gradually increased, the mode determiner 560 may determine a function shape change mode, in which case the shape of the adjustment coefficient function may be changed to a narrower or sharper shape based on a point at which a bio-information variation is zero. The shape of the adjustment coefficient function may be pre-defined appropriately according to each shape change mode.

Further, if a level of change of reference bio-information values (e.g., cuff pressure) and/or a level of change of reference features is less than a threshold, the mode determiner 560 may determine a function shape change mode, and may change the shape of the adjustment coefficient function so that the adjustment coefficient may be closer to a constant value of 1. In addition, if a level of change of the reference bio-information values (e.g., cuff pressure) and/or a level of change of the reference features is greater than or equal to a threshold, the mode determiner 560 may not change the shape of the adjustment coefficient function; and if the level of change of the reference bio-information values (e.g., cuff pressure) and/or the level of change of the reference features is greater than or equal to a threshold and the number of times of calibration is gradually increased, the mode determiner 560 may change the shape of the adjustment coefficient function to a narrower or sharper shape based on a point at which a bio-information variation is zero.

Moreover, the mode determiner 560 may determine the mode by using both the level of change of the reference bio-information values and the level of change of the reference features. For example, the mode determiner 560 may determine the mode by comparing the levels of change with each threshold and using the result of comparison, or by combining the level of change of the reference bio-information values with the level of change of the reference features and comparing the result of combination with each threshold.

Further, the mode determiner 560 may define two or more thresholds, and may apply both the ON/OFF mode and the shape change mode. For example, if any one or a combination of two or more of calibration information items is less than a first threshold, the mode determiner 560 may determine an OFF mode; if any one or a combination of two or more of calibration information items is greater than or equal to the first threshold and is less than a second threshold, the mode determiner 560 may determine the shape change mode, and if any one or a combination of two or more of calibration information items is greater than or equal to the second threshold, the mode determiner 560 may determine an ON mode so that a pre-defined adjustment coefficient function may be used as it is. However, the determination of mode is not limited thereto, and may be defined in various manners.

Figure 6:
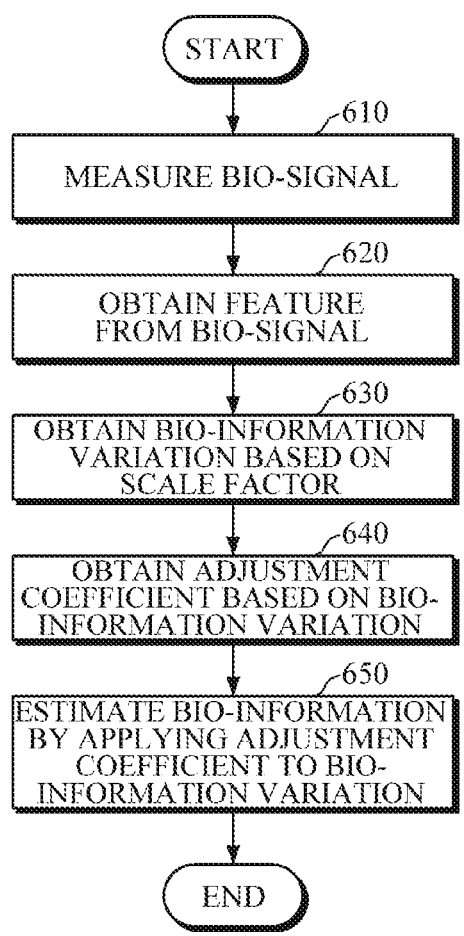
FIG. 6 is a flowchart illustrating a method of estimating bio-information according to an example embodiment.

FIG. 6 is a flowchart illustrating a method of estimating bio-information according to an example embodiment. The method of FIG. 6 may be an example of a bio-information estimating method performed by the bio-information estimation apparatus 100a or 100b of FIG. 1A or 1B.

Upon receiving a request for estimating bio-information, the bio-information estimating apparatus 100a or 100b may measure a bio-signal in operation 610. The bio-information estimating apparatus may measure the bio-signal upon receiving the request for estimating bio-information from a user or an external device, or in response to the occurrence of a predetermined measurement event. In this case, the bio-signal may include a photoplethysmogram (PPG) signal, but is not limited thereto.

Then, the bio-information estimating apparatus may obtain a feature from the bio-signal in operation 620. In this case, the feature may be obtained by analyzing a waveform of the bio-signal, and may be a value that is obtained by linearly/non-linearly combining any one or two or more of a time/amplitude of a maximum/minimum point, a time/amplitude of a position of a constituent pulse waveform, an area of the bio-signal, a heart rate, and the like, and which has a high correlation with bio-information to be obtained.

Subsequently, the bio-information estimating apparatus may obtain a bio-information variation based on the obtained feature and a scale factor in operation 630. For example, the bio-information estimating apparatus may obtain the bio-information variation by multiplying a variation between features, obtained in operation 620 for estimating bio-information at a current time compared to a reference feature obtained at a reference time, e.g., a steady-state calibration time, by a scale factor. In this case, the scale factor may be a fixed value that may be applied so that the feature variation, having a high correlation with the estimated bio-information variation, may be adjusted to be closer to an actual bio-information variation measured by an external bio-information measuring device.

Next, the bio-information estimating apparatus may obtain an adjustment coefficient based on the bio-information variation in operation 640. In this case, the adjustment coefficient may be a value for adaptively adjusting the scale factor, which is a fixed constant value, according to various circumstances e.g., various changing aspects of the bio-information variation. For example, the bio-information estimating apparatus may obtain the adjustment coefficient by using the bio-information variation, obtained in operation 630, as an input.

The adjustment coefficient function may output an adjustment coefficient for properly adjusting, e.g., increasing, the scale factor according to a sign and/or a magnitude of the bio-information variation. For example, the adjustment coefficient function may be defined to output an adjustment coefficient having a gradually increasing trend, so that as an absolute value of the bio-information variation decreases, i.e., is gradually closer to zero, the scale factor may relatively increase further. However, the adjustment coefficient function is not limited thereto, and may output an adjustment coefficient having an equal/similar value by gradually reducing an increase in the scale factor as the bio-information variation is closer to zero. Further, the adjustment coefficient function may be defined to output an adjustment coefficient that gradually decreases, so that as an absolute value of the bio-information variation gradually increases, the scale factor may relatively increase less; and which is gradually closer to 1, so that the scale factor may be maintained at an original value or a similar value after a predetermined point.

Then, the bio-information estimating apparatus may estimate bio-information in operation 650 by applying the adjustment coefficient, obtained in operation 640, to the bio-information variation obtained in operation 630. For example, by multiplying the bio-information variation, which is obtained by applying the scale factor to the feature variation, by the adjustment coefficient, the bio-information estimating apparatus may further correct the bio-information variation so that the bio-information variation may be closer to an actual reference bio-information variation, and may obtain an estimated bio-information value by adding an offset to the corrected variation. The estimated bio-information value may be provided to a user by various methods using a display, an audio output interface, a haptic interface, and the like. In addition, the bio-information estimating apparatus may determine a user's health condition based on the estimated bio-information, and may provide a warning or a response action to the user based on the determination.

Figure 7:
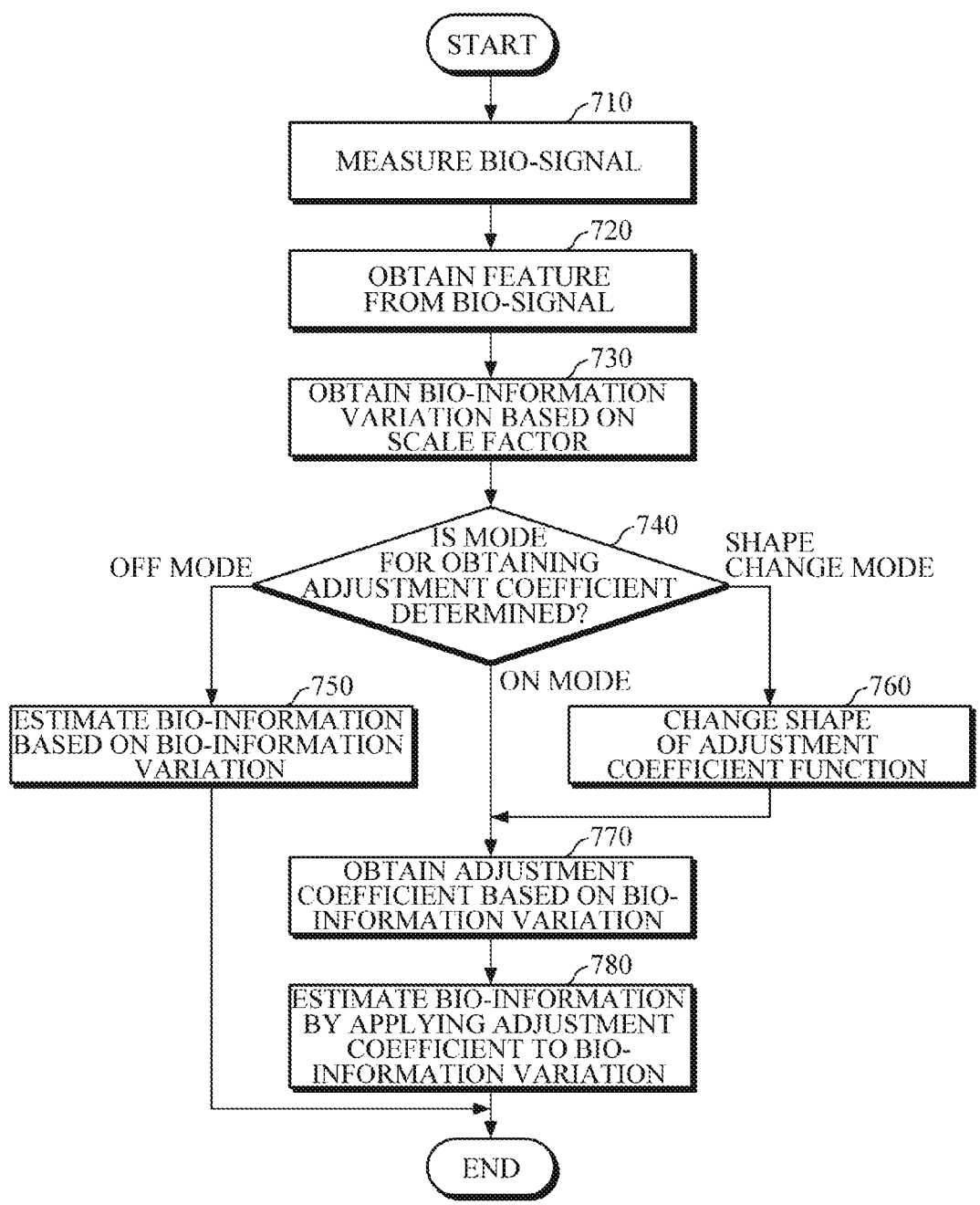
FIG. 7 is a flowchart illustrating a method of estimating bio-information according to an example embodiment.

FIG. 7 is a flowchart illustrating a method of estimating bio-information according to an example embodiment. The method of FIG. 7 may be an example of a bio-information estimating method performed by the bio-information estimating apparatus 100a or 100b of FIG. 1A or 1B, which is described above in detail such that the following description will be briefly made.

Upon receiving a request for estimating bio-information, the bio-information estimating apparatus 100a or 100b may measure a bio-signal in operation 710, may obtain a feature from the bio-signal in operation 720, and may obtain a bio-information variation based on the obtained feature and a scale factor in operation 730.

Then, the bio-information estimating apparatus 100a or 100b may determine a mode for obtaining an adjustment coefficient based on calibration information in operation 740. For example, the calibration information may include a number of times of calibration performed before a current time of estimating bio-information, a level of change between reference bio-information values, a level of change between reference features, and the like. Further, the mode may include an ON/OFF mode for applying or not applying an adjustment coefficient according to predetermined criteria, and/or a shape change mode for changing a shape of an adjustment coefficient function.

For example, if a number of times of calibration performed before a current time of estimating bio-information is less than a threshold, or if a level of change of reference bio-information values or a level of change of reference features is lower than a threshold, the bio-information estimating apparatus 100a or 100b may determine an OFF mode; and if the number of times or the level of change is greater than or equal to the threshold, the bio-information estimating apparatus 100a or 100b may determine an ON mode.

Upon determining the OFF mode in operation 740, the bio-information estimating apparatus 100a or 100b may estimate bio-information in operation 750 based on the bio-information variation obtained in operation 730 without obtaining the adjustment coefficient in operation 770. In this case, as represented by the above Equation 1, the bio-information estimating apparatus 100a or 100b may obtain a bio-information estimation value by adding a reference bio-information value at a calibration time as an offset to the bio-information variation. Here, the reference bio-information value, used as an offset, may be reference bio-information obtained by an external bio-information measuring device at an initial calibration time or at a calibration time closest to the current time when calibration is performed a plurality of times. However, the reference bio-information value is not limited thereto, and may be a statistical value (e.g., a mean value, a median value, a maximum value, a minimum value, etc.) of the reference bio-information values obtained when calibration is performed a plurality of times.

Upon determining the ON mode in operation 740 as a mode for obtaining an adjustment coefficient, the bio-information estimating apparatus 100a or 100b may obtain an adjustment coefficient in operation 770 based on the bio-information variation, obtained in operation 730, as an input to an adjustment coefficient function, and may estimate bio-information by applying the adjustment coefficient to the bio-information variation in operation 780.

In addition, upon determining a shape change mode in operation 740 as a mode for obtaining an adjustment coefficient, the bio-information estimating apparatus 100a or 100b may change the shape of the adjustment coefficient function in operation 760. For example, if a number of times of calibration performed before the current time of estimating bio-information is less than a threshold, or if a level of change of reference bio-information or a level of change of reference features is lower than a threshold, the bio-information estimating apparatus 100a or 100b may determine the shape change mode for changing the shape of the adjustment coefficient function. For example, if the number of times of calibration is greater than or equal to a threshold and is gradually increased, the bio-information estimating apparatus 100a or 100b may change the shape of the adjustment coefficient function to a narrower or sharper shape based on (i.e., adjacent to) a point at which a bio-information variation is zero.

Then, upon changing the shape of the adjustment coefficient function in operation 760, the bio-information estimating apparatus 100a or 100b may obtain an adjustment coefficient based on the changed adjustment coefficient function in operation 770, and may estimate bio-information by applying the obtained adjustment coefficient to the bio-information variation in operation 780.

In the determining of the mode for obtaining the adjustment coefficient in operation 740, it may be predetermined to determine only the ON/OFF mode or only the shape change mode. However, the determination of mode is not limited thereto; and upon defining two or more thresholds, if one or a combination of two or more of the calibration information items is less than a first threshold, the bio-information estimating apparatus 100a or 100b may determine the OFF mode; if one or a combination of two or more of the calibration information items is between the first threshold and a second threshold, the bio-information estimating apparatus 100a or 100b may determine the shape change mode; and if one or a combination of two or more of the calibration information items is greater than or equal to the second threshold, the bio-information estimating apparatus 100a or 100b may determine the ON mode.

Figure 8:
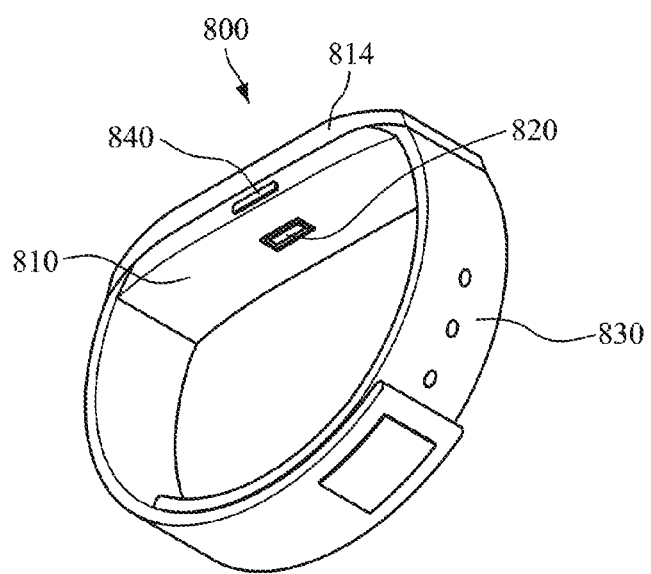
FIG. 8 is a diagram illustrating a wearable device according to embodiments.

FIG. 8 is a diagram illustrating a wearable device according to an example embodiment. The embodiments of the bio-information estimating apparatuses 100a and 100b described above may be mounted in a smart watch worn on a wrist or a smart band-type wearable device. However, these are examples for convenience of explanation, and the bio-information estimating apparatuses 100a and 100b may be mounted in a smartphone, a tablet PC, a laptop computer, a desktop computer, and the like.

Referring to FIG. 8, the wearable device 800 includes a main body 810 and a strap 830.

The main body 810 may be formed to have various shapes, and may include parts that are mounted inside or outside of the main body 810 to perform the aforementioned function of estimating bio-information as well as various other functions. A battery may be embedded in the main body 810 or the strap 830 to supply power to various parts of the wearable device 800.

The strap 830 may be connected to the main body 810. The strap 830 may be flexible to be bent around a user's wrist. The strap 830 may be bent in a manner that allows the strap 830 to be detached from the user's wrist or may be formed as a band that is not detachable. Air may be injected into the strap 830 or an airbag may be included in the strap 830, so that the strap 830 may have elasticity according to a change in pressure applied to the wrist, and the change in pressure of the wrist may be transmitted to the main body 810.

The main body 810 may include a sensor 820 for measuring a bio-signal. The sensor 820 may be mounted on a rear surface of the main body 810, which comes into contact with the upper portion of a user's wrist, and may include a light source for emitting light onto the skin of the wrist and a detector for detecting light scattered or reflected from the object. The sensor 820 may further include a contact pressure sensor for measuring contact pressure applied by the object.

A processor may be mounted in the main body 810. The processor may be electrically connected to various parts, mounted in the wearable device 800, to control operations thereof. Further, the processor may estimate bio-information by using bio-signals measured by the sensor 820. As described above, the processor may obtain features from the bio-signals, and may obtain a bio-information variation by using the obtained features and the scale factor. In addition, the processor may obtain an adjustment coefficient for adjusting the scale factor based on the bio-information variation, and may estimate bio-information by further applying the obtained adjustment coefficient.

In the case in which the processor includes a contact pressure sensor, the processor may monitor a contact state of the object based on contact pressure between the wrist and the sensor 820, and may provide guidance on a contact position and/or a contact state to a user through a display.

Further, the main body 810 may include a storage that stores a processing result of the processor and various types of information. In this case, various types of information may include reference information associated with estimating bio-information, as well as information associated with functions of the wearable device 800.

In addition, the main body 810 may also include a manipulator 840 that receives a user's control instruction and transmits the received control instruction to the processor. The manipulator 840 may include a power button to input an instruction to turn on/off the wearable device 800.

A display 814 may be mounted on a front surface of the main body 810, and may include a touch panel for touch input. The display may receive a touch input from a user, may transmit the received touch input to the processor, and may display a processing result of the processor. For example, the display 814 may display a bio-information estimation value and warning/alarm information.

Moreover, a communication interface, provided for communication with an external device such as a user's mobile terminal, may be mounted in the main body 810. The communication interface may transmit an estimation result of bio-information to an external device, e.g., a user's smartphone, to display the result to the user. However, the communication interface is not limited thereto, may transmit and receive various types of information.

Figure 9:
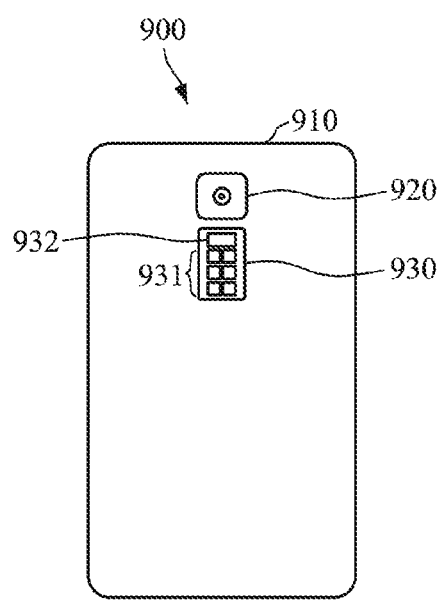
FIG. 9 is a diagram illustrating a smart device according to an example embodiment.

FIG. 9 is a diagram illustrating a smart device according to an example embodiment. In this case, the smart device may be a smartphone, a tablet PC, and the like, and may include the bio-information estimating apparatuses 100a and 100b described above.

Referring to FIG. 9, the smart device 900 includes a main body 910 and a sensor 930 mounted on one surface of the main body 910. In this case, the sensor 930 may include a pulse wave sensor including at least one or more light sources 931 and a detector 932. As illustrated in FIG. 9, the sensor 930 may be mounted on a rear surface of the main body 910, but is not limited thereto, and may be configured in combination with a fingerprint sensor or a touch panel mounted on a front surface of the main body 910.

In addition, a display may be mounted on a front surface of the main body 910. The display may visually display an estimation result of bio-information and the like. The display may include a touch panel, and may receive various types of information input through the touch panel and transmit the received information to the processor.

Moreover, an image sensor 920 may be mounted in the main body 910. When a user's finger approaches the sensor 930 to measure a pulse wave signal, the image sensor 920 may capture an image of the finger and may transmit the captured image to the processor. In this case, based on the image of the finger, the processor may identify a relative position of the finger with respect to an actual position of the sensor 930, and may provide the relative position of the finger to the user through the display, to guide measurement of pulse wave signals with improved accuracy.

As described above, the processor may estimate bio-information based on bio-signals measured by the sensor 930. In this case, the processor may estimate bio-information more accurately by obtaining an adjustment coefficient based on a bio-information variation and by adaptively adjusting the scale factor as described above.

The embodiments can be realized as a computer-readable code written on a non-transitory computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments for realizing the embodiments can be easily deduced by one of ordinary skill in the art.

The inventive concepts have been described herein with regard to the example embodiments. However, it will be obvious to those skilled in the art that various changes and modifications can be made without changing technical ideas and features of the present disclosure. Thus, it is clear that the above-described example embodiments are illustrative in all aspects and are not intended to limit the present disclosure.

What is claimed is:

1. An apparatus for estimating bio-information, the apparatus comprising:
   a bio-signal sensor configured to measure a bio-signal from an object at an estimation time to monitor a health state of the object;
   at least one of a strap, a fingerprint sensor, or a touch panel;
   a memory configured to store an adjustment coefficient function;
   an image sensor configured to capture an image of the object; and
   a processor configured to:
      obtain a feature based on the measured bio-signal at the estimation time;
      obtain a bio-information variation based on a variation of the obtained feature in comparison to a feature that is obtained based on a bio-signal measured at a reference time;
      adaptively change an adjustment coefficient based on the bio-information variation while the bio-signal sensor is monitoring the health state of the object, using the adjustment coefficient function stored in the memory so that as an absolute value of the bio-information variation decreases, the adjustment coefficient increases, and as the absolute value of the bio-information variation increases, the adjustment coefficient decreases or has a constant value after a predetermined point of the absolute value of the bio-information variation;
      estimate the bio-information with improved accuracy to prevent danger to a user's health, the user including the object, by applying the adjustment coefficient to the bio-information variation;
      determine whether the estimated bio-information falls outside a predetermined normal range;
      when the estimated bio-information has been determined to fall outside the predetermined normal range, control an alarm to be activated;
      based on the captured image received from the image sensor, detect a relative position of the object with respect to an actual position of the bio-signal sensor; and
      based on the detected relative position of the object, direct a display to display the relative position of the object to the user to guide estimation of the bio-information with improved accuracy;
   wherein the bio-signal sensor comprises:
      a light source configured to emit light onto the object; and
      a detector configured to detect light that is scattered from the object.

2. The apparatus of claim 1, wherein the processor is further configured to obtain the bio-information variation by multiplying, by a scale factor, the variation of the obtained feature.

3. The apparatus of claim 1, wherein the adjustment coefficient function outputs the adjustment coefficient to be applied to the obtained bio-information variation to adjust the obtained bio-information variation so that the bio-information variation is closer to a reference bio-information variation.

4. The apparatus of claim 1, wherein the adjustment coefficient function is defined using either one or both of a linear function and a non-linear function for intervals that are divided based on either one or both of a sign and a magnitude of the bio-information variation.

5. The apparatus of claim 4, wherein the adjustment coefficient function is defined such that:
   in an interval in which the bio-information variation has a negative sign and the magnitude of the bio-information variation is less than a first threshold, the adjustment coefficient is maintained at a first value;
   in an interval in which the bio-information has the negative sign and the magnitude of the bio-information variation ranges from the first threshold to a second threshold greater than the first threshold, the adjustment coefficient linearly or non-linearly increases from the first value to a second value;
   in an interval in which the bio-information has the negative sign and the magnitude of the bio-information variation ranges from the second threshold to zero, the adjustment coefficient is maintained at the second value, or linearly or non-linearly increases from the second value to a third value;
   in an interval in which the bio-information variation has a positive sign and the magnitude of the bio-information variation ranges from zero to a third threshold, the adjustment coefficient is maintained at a fourth value, or linearly or non-linearly decreases from the fourth value to a fifth value;
   in an interval in which the bio-information has the positive sign and the magnitude of the bio-information variation ranges from the third threshold to a fourth threshold greater than the third threshold, the adjustment coefficient linearly or non-linearly decreases from the fourth value to a sixth value or from the fifth value to the sixth value; and
   in an interval in which the bio-information has the positive sign and the magnitude of the bio-information variation is greater than the fourth threshold, the adjustment coefficient is maintained at the sixth value.

6. The apparatus of claim 5, wherein each of the first threshold, the second threshold, the third threshold, the fourth threshold, the first value, the second value, the third value, the fourth value, the fifth value, the sixth value, the linear function and the non-linear function are defined based on any one or any combination of a computing performance, types of the bio-information to be estimated, user characteristics, and a surrounding environment.

7. The apparatus of claim 1, wherein the processor is further configured to obtain a bio-information estimation value by multiplying the obtained bio-information variation by the obtained adjustment coefficient and by adding an offset to the bio-information variation multiplied by the obtained adjustment coefficient.

8. The apparatus of claim 1, wherein the processor is further configured to obtain the feature by combining any or any combination of a shape of a waveform of the measured bio-signal, a time value and an amplitude value of a maximum point of the measured bio-signal, a time value and an amplitude value of a minimum point of the measured bio-signal, a time value and an amplitude value of a position of a pulse waveform component included in the measured bio-signal, and an area of the measured bio-signal.

9. The apparatus of claim 1, wherein the bio-information comprises any one or any combination of a blood pressure, a vascular compliance, an arterial stiffness, a stress index, a degree of fatigue, a skin elasticity, and a skin age.

10. The apparatus of claim 1, wherein the processor is further configured to:
control the memory to store a level of change between reference features that are obtained at each of a plurality of calibrations, and information of a number of the plurality of calibrations that have been conducted until a current time, and
switch an OFF mode in which a process of obtaining the adjustment coefficient is deactivated, to an ON mode in which the process of obtaining the adjustment coefficient is activated, in response to the number of a plurality of calibration times reaching a preset number.

11. The apparatus of claim 1, wherein
the strap is configured to maintain contact of the bio-signal sensor with the object,
the fingerprint sensor is configured to detect a fingerprint of the user including the object, and
the touch panel is configured to receive touch input from the user including the object.

12. A method of estimating bio-information, the method comprising:
measuring a bio-signal from an object by a bio-signal sensor at an estimation time to monitor a health state of the object;
obtaining a feature based on the measured bio-signal at the estimation time;
obtaining a bio-information variation based on a variation of the obtained feature in comparison to a feature that is obtained based on a bio-signal measured at a reference time;
adaptively changing an adjustment coefficient based on the bio-information variation while the bio-signal sensor is monitoring the health state of the object, using an adjustment coefficient function stored in a memory, so that as an absolute value of the bio-information variation decreases, the adjustment coefficient increases, and as the absolute value of the bio-information variation increases, the adjustment coefficient decreases or has a constant value after a predetermined point of the absolute value of the bio-information variation;
estimating the bio-information with improved accuracy to prevent danger to a user's health, the user including the object, by applying the adjustment coefficient to the bio-information variation;
determining whether the estimated bio-information falls outside a predetermined normal range;
when the estimated bio-information has been determined to fall outside the predetermined normal range, controlling an alarm to be activated;
receiving a captured image of the object from an image sensor;
based on the captured image, detecting a relative position of the object with respect to an actual position of the bio-signal sensor; and
based on the detected relative position of the object, directing a display to display the relative position of the object to the user to guide estimation of the bio-information with improved accuracy;
wherein the method is performed by an apparatus including at least one of a strap, a fingerprint sensor, or a touch panel;
wherein measuring the bio-signal comprises:
directing a light source emit light onto the object; and
receiving from a detector detected light that is scattered from the object.

13. The method of claim 12, wherein the obtaining of the bio-information variation comprises obtaining the bio-information variation by multiplying, by a scale factor, the variation of the obtained feature.

14. The method of claim 12, wherein the adjustment coefficient function outputs the adjustment coefficient to be applied to the obtained bio-information variation to adjust the obtained bio-information variation so that the bio-information variation is closer to a reference bio-information variation.

15. The method of claim 12, wherein the adjustment coefficient function is defined using either one or both of a linear function and a non-linear function for intervals that are divided based on either one or both of a sign and a magnitude of the bio-information variation.

16. The method of claim 12, wherein the estimating of the bio-information comprises obtaining a bio-information estimation value by multiplying the obtained bio-information variation by the obtained adjustment coefficient and by adding an offset to the bio-information variation multiplied by the obtained adjustment coefficient.

17. The method of claim 12, wherein the obtaining of the feature comprises obtaining the feature by combining any or any combination of a shape of a waveform of the measured bio-signal, a time value and an amplitude value of a maximum point of the measured bio-signal, a time value and an amplitude value of a minimum point of the measured bio-signal, a time value and an amplitude value of a position of a pulse waveform component included in the measured bio-signal, and an area of the measured bio-signal.

18. The method of claim 12, wherein
the strap is configured to maintain contact of the bio-signal sensor with the object,
the fingerprint sensor is configured to detect a fingerprint of the user including the object, and
the touch panel is configured to receive touch input from the user including the object.

* * * * *